United States Patent [19]

Richard et al.

[11] Patent Number: 5,295,953

[45] Date of Patent: Mar. 22, 1994

[54] METHOD AND APPARATUS FOR EXTRACORPOREAL SEPARATION OF FLUOROCHEMICALS FROM WHOLE BLOOD OF A PATIENT

[75] Inventors: Thomas J. Richard, University City, Mo.; Donald W. Schoendorfer, Santa Anna, Calif.; Robert J. Kaufman, University City; Thomas H. Goodin, Manchester, both of Mo.

[73] Assignees: HemaGen/PFC, St. Louis, Mo.; Baxter Health Care Corporation, Santa Anna, Calif.

[21] Appl. No.: 888,987

[22] Filed: May 26, 1992

[51] Int. Cl.$^5$ ............................................ A61N 1/03
[52] U.S. Cl. ........................................ 604/5; 604/4; 604/49
[58] Field of Search ................... 604/4, 5, 6, 19, 27, 604/28, 48, 49, 56; 424/5

[56] References Cited

U.S. PATENT DOCUMENTS

| | | | |
|---|---|---|---|
| 3,916,892 | 11/1975 | Latham, Jr. | 604/272 X |
| 3,975,512 | 8/1976 | Long | 424/5 |
| 4,146,172 | 3/1979 | Cullis et al. | 604/6 X |
| 4,683,889 | 8/1987 | Edelson | 604/6 X |
| 4,708,714 | 11/1987 | Larsson et al. | 604/5 |
| 4,834,890 | 5/1989 | Brown et al. | 604/6 X |
| 4,993,415 | 2/1991 | Long | 424/5 X |

FOREIGN PATENT DOCUMENTS 231070  5/1987  European Pat. Off. .
231091  6/1987  European Pat. Off. .
8910118 11/1989 World Int. Prop. O. .

OTHER PUBLICATIONS

Agishi, T. et al, "(Pyridoxalated Hemoglobin)-(Polyoxyethylene) Conjugate Solution as Blood Substitute for Normothermic Whole Body Rinse-Out", *Biomat., Art. Cells, Art. Org.*, 16(1-3), pp. 261-270 (1988).
Agishi, T. et al, "Retrieval of Artificial Blood Cells (Perfluorochemical) From Whole Blood", Trans. Am. Sec. Artif. Intern. Organs, vol. XXIX, pp. 456-459 (1983).
Lutz, Joachim, "Effect of Perfluorochemicals on Host Defense, Especially on the Reticuloendothelial System", *Int'l Anesthesiology Clinics*, (23), pp. 63-93 (1985). Yokoyama, Kazumasa, "Preparation of perfluorodecaline emulsion, an approach to the red cells substitute", Federation Proceedings, vol. 34, No. 6, pp. 1478-1483 (May 1975).

*Primary Examiner*—Danton D. DeMille
*Assistant Examiner*—Sam Rimell
*Attorney, Agent, or Firm*—Wood, Herron & Evans

[57] ABSTRACT

Methods and apparatus for practical extracorporeal separation of fluorochemicals from clinically fluorochemical-containing whole blood of a patient. The methods incorporate centrifugal apheresis devices, preferably with low extracorporeal volumes, that provide a means for continuously removing separated fluorochemical-enriched fractions from the centrifuge during processing and return of whole blood-enriched fractions to the patient.

12 Claims, 6 Drawing Sheets

METHOD AND APPARATUS FOR EXTRACORPOREAL SEPARATION OF FLUOROCHEMICALS FROM WHOLE BLOOD OF A PATIENT

TECHNICAL FIELD OF THE INVENTION

This invention relates to methods for separating fluorochemicals from whole blood. More particularly, this invention relates to extracorporeal separation methods that remove a fluorochemical enriched fraction from fluorochemical-containing whole blood by means of a centrifugal apheresis device. The methods of this invention are useful in a variety of medical applications that use fluorochemical blood substitutes, particularly where extracorporeal removal of the fluorochemical from blood is desired as an alternative to natural excretion.

BACKGROUND OF THE INVENTION

Fluorochemicals, and especially perfluorochemicals, are known to be chemically and pharmaceutically inert and to be capable of dissolving and transporting large amounts of oxygen. Because of these properties, fluorochemical emulsions have been proposed as intravenously acceptable oxygen transport agents, and as "artificial blood" or "red blood cell substitutes" for human and animal patients. Fluorochemical emulsions thus have potential application in for example, emergency treatment, elective, emergency and trauma surgery, myocardial infarct treatment, coronary balloon angioplasty, stroke treatment, intraperitoneal oxygenation, and surgery involving hemodilution. Fluorochemical emulsions also have potential use as contrast agents for various imaging modalities such as nuclear magnetic resonance, ultrasound and x-ray. See European Patent Publication 231 091 and PCT publication W089/10118. In addition, fluorochemical emulsions have been proposed as vehicles for supplying oxygen to the lungs in the field of liquid breathing. Fluorochemical emulsions thus have potential application in for example, the treatment of respiratory distress syndrome, cystic fibrosis, ventilator distress, pneumonia, edema and other pulmonary complications. In liquid breathing applications, fluorochemical is also transported to the bloodstream.

If not artificially removed from the patient's blood, fluorochemicals are cleared into the cells of the reticuloendothelial system (RES) over two to six day period, depending upon the dosage. See, e.g., K. Yokoyma et al., "Preparation of Perfluorodecalin Emulsion, An Approach to the Red Cells Substitute," *Fed. Proc.*, (34), pp. 1478-83 (1975). However, natural elimination, via the RES, may result in retention of some of the fluorochemical in the patient's organs. See J. Lutz, "Effect of Perfluorochemicals on Host Defense, Especially on the Reticuloendothelial System," *Int'l Anesthesiology Clinics*, (23), 63-93 (1985). Therefore, development of an extracorporeal method for removal of fluorochemical from blood is desired as an improved alternative to natural excretion.

One approach to separation of fluorochemical from whole blood is referred to in T. Agishi et al., "Retrieval of Artificial Blood Cells (Perfluorochemical) from Whole Blood," *Trans. Am. Soc. Artif. Organs*, (20), pp. 456-59 (1983). Agishi refers to the attempted separation of a fluorochemical emulsion from the whole blood of dogs by batch centrifugation with a Haemonetics V-50 apheresis device (manufactured by Haemonetics Corporation, Braintree, Mass.). Agishi states that the Haemonetics V-50 centrifugation bowl accumulated trapped fluorochemical which was very difficult to remove. This difficulty arose even though the greatest volume of fluorochemical-containing blood processed was only 2.5 liters at a very low initial hematocrit of 4% and a low initial fluorocrit of 8% (cc of fluorochemical per 100 ml of blood). Agishi does not suggest a clinically practical method of separating fluorochemical from whole blood using batch centrifugal apheresis with the Haemonetics V-50. Another attempt at using the Haemonetics V-50 in the separation of fluorochemical emulsion from blood is referred to in T. Agishi et "(Pyridoxalated Hemoglobin)—(Polyoxethylene) Conjugate Solution As Blood Substitute For normothermic Whole Body Rinse-Out," *Biomat., Art. Cells. Art Org.*, 16(1-3), 261-270 (1988). There, an attempt was made to reduce the level of pathogenic substances (e.g. digoxin) in the blood of dogs by replacing approximately 2,000 to 2,500 ml of blood with the fluorochemical emulsion Fluosol-DA. Agishi reported that batch centrifugation using the Haemonetics V-50 removed only 60 to 70% of the fluorochemical from the dogs, leaving a residual amount stated to be beyond the recommended maximum. Again, there was no suggestion of a clinically practical method of separating fluorochemical from whole blood. The Haemonetics V-50 centrifugal apheresis device performs batch separation on discrete quantities of blood. Batch centrifugal apheresis devices, such as the Haemonetics V-50, operate in a cycle in the following manner. The first part of the cycle, called the "draw cycle", draws blood into a spinning centrifuge bowl where the components are separated by centrifugal force. Heavier fractions are spun to the outer wall of the centrifuge, while lighter fractions move to the center. When used to separate fluorochemical from whole blood, the Haemonetics V-50 spins the heaviest component, the fluorochemical-enriched fraction, to the outer wall of the centrifuge and the lighter component, the whole blood-enriched fraction to the center of the centrifuge. Once the bowl is full of fluid, continued pumping of the blood fluorochemical mixture displaces the whole blood enriched fraction through the exit port. The next part of the cycle, called the "return cycle", occurs when the centrifuge bowl is full of the fluorochemical-enriched fraction. During the return cycle, the remaining heavier components in the bowl must be drawn off to make way for the next batch. Unfortunately, separated fluorochemical cannot be removed from the centrifuge system as it is too viscous to be drawn off and therefore remains in the centrifuge bowl for the duration of processing. Eventually the fluorochemical-enriched fraction completely fills the centrifuge bowl preventing flow into the bowl, and thus further processing. Therefore, the amount of fluorochemical that can be separated from whole blood by the Haemonetics V-50, or any batch processing device, is inherently limited by the volume of the centrifuge bowl. The Haemonetics V-50 centrifuge can be outfitted with bowls having volumes of 125, 225 or 350 ml.

Another centrifugal apheresis device, the Fenwal CS-3000 Plus (Baxter Healthcare Corporation, Deerfield, Ill.), equipped with a centrifuge belt, is similarly limited by its centrifuge belt volume of about 250 ml. Although the CS-3000 is not a batch processor, upon experimentation it has been shown by the inventors of the invention described hereinafter to share with the Haemonetics V-50 the same characteristic of production of an excessively high viscosity fluorochemical fraction. The fluorochemical fraction essentially clogged flow through the apparatus and the CS-3000 also failed. Because the separation methods characterized by the Haemonetics V-50 and the Fenwal CS-3000 Plus generally result in fluorochemical clogging the apparatus, they fail to achieve clinically useful separation of fluorochemical from whole blood, which generally requires that all of a patient's blood be processed.

In addition to fluorochemical clogging of the centrifuge bowl, the above centrifugal apheresis devices often require relatively large operating volumes, above 250 ml. This also limits their utility in applications for the separation of fluorochemicals from whole blood. At first glance, a larger operating volume may appear to be a solution to the fluorochemical clogging problem since more fluorochemical could be separated before flow into the centrifuge stopped. In practice, however, taking significant blood volumes from patients can cause them to become hypotensive. Furthermore, most emergency and trauma patients, and many surgical patients, are already hypotensive, and taking a large extracorporeal volume from them for centrifugation is contraindicated.

In brief summary, the possibility of expanding the applications of fluorochemicals in medicine by using a fluorochemical blood substitute for a short time and then extracorporeally removing it from a patient's blood has not been achieved by the use of known centrifugal apheresis devices or any other methods.

SUMMARY OF THE INVENTION

This invention is directed to a method and an apparatus for extracorporeally removing fluorochemical from fluorochemical-containing blood of a patient. The method involves withdrawing a therapeutically acceptable extracorporeal volume of the fluorochemical-containing whole blood from the patient. The withdrawn blood is continuously passed through a continuous centrifuge device for removal of the fluorochemical and return of the blood to the patient at a therapeutically acceptable flow rate. In the device, the withdrawn blood is centrifugally separated at a therapeutically acceptable spin rate into a fluorochemical-enriched fraction and a whole blood-enriched fraction. The fluorochemical-enriched fraction is removed from the centrifuge device to prevent build up of fluorochemical in the device and the whole blood-enriched fraction is returned to the patient. In a preferred form, the fluorochemical-enriched fraction and whole blood-enriched fraction are continuously removed from the centrifuge device during one uninterrupted cycle.

This invention provides, for the first time, a method and apparatus for successful removal of fluorochemical from a patient's blood stream. This invention allows for the separation of fluorochemicals from clinically useful quantities of fluorochemical-containing whole blood. It also overcomes the problem of fluorochemical clogging of the centrifuge devices and other problems referred to above in the background of this invention.

In addition, the preferred embodiments of this invention reduce the risk of hypotension and death to the emergency, trauma or surgical patient by removing very low extracorporeal volumes of blood during the centrifugation and fluorochemical separation. This invention accomplishes virtually complete separation of fluorochemical from blood without damage to red blood cells, white blood cells, or platelets. It also provides a method for safe fluorochemical treatment of patients with virtually no limitation on dose.

The invention, its advantages and various embodiments will be further understood with reference to the drawings and following detailed description.

DETAILED DESCRIPTION OF THE INVENTION

The methods of this invention separate fluorochemicals from clinically useful quantities of fluorochemical-containing whole blood using continuous centrifuge devices, with fluorochemical separation potential and, preferably, low processing volumes.

Figure 1:
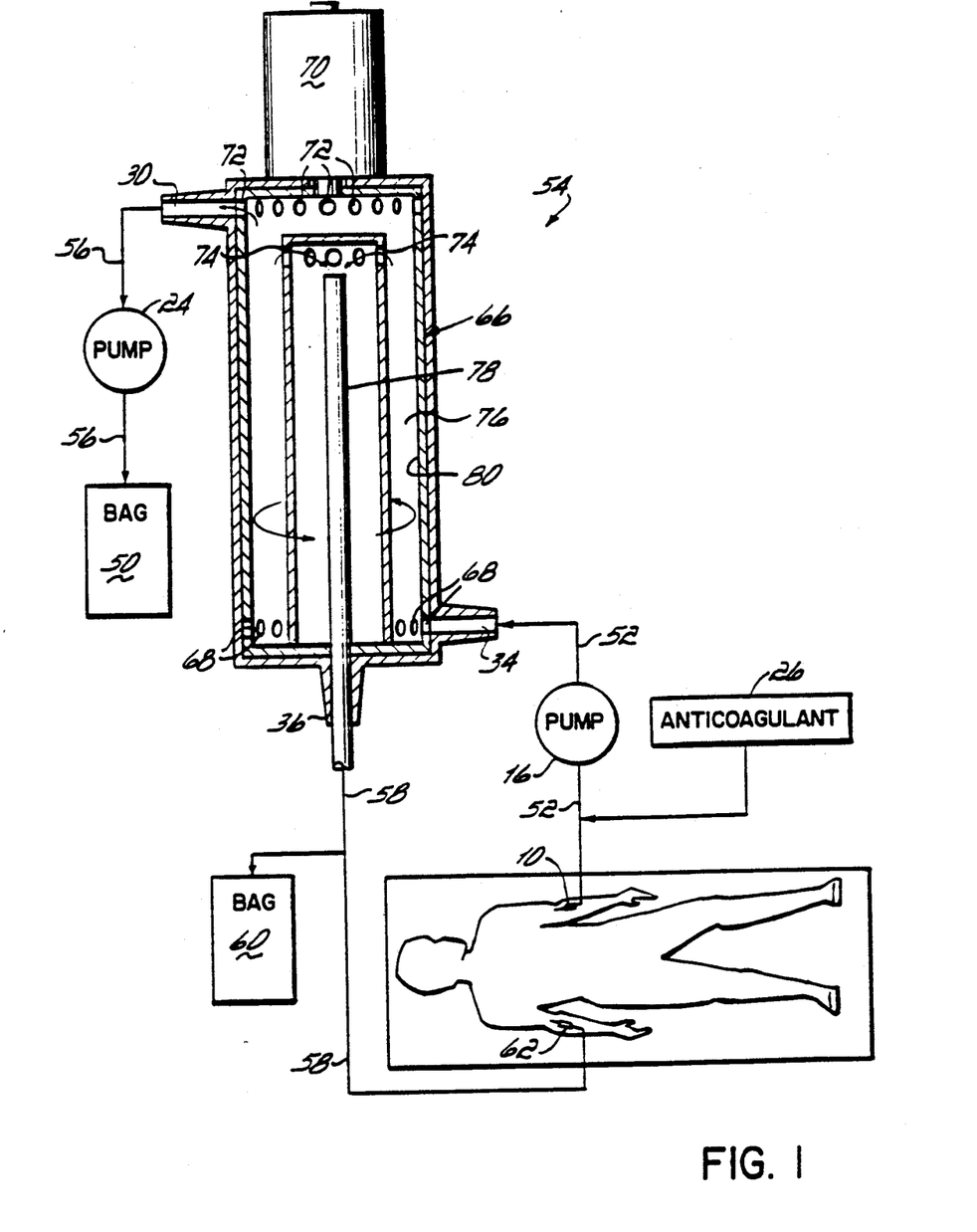
FIG. 1 is a diagrammatic view of a Fenwal Autopheresis-C Plateletcell separation device of Baxter Healthcare Corporation, modified for continuous removal of a fluorochemical-enriched fraction from fluorochemical-containing whole blood of a patient for use in this invention.
Figure 2:
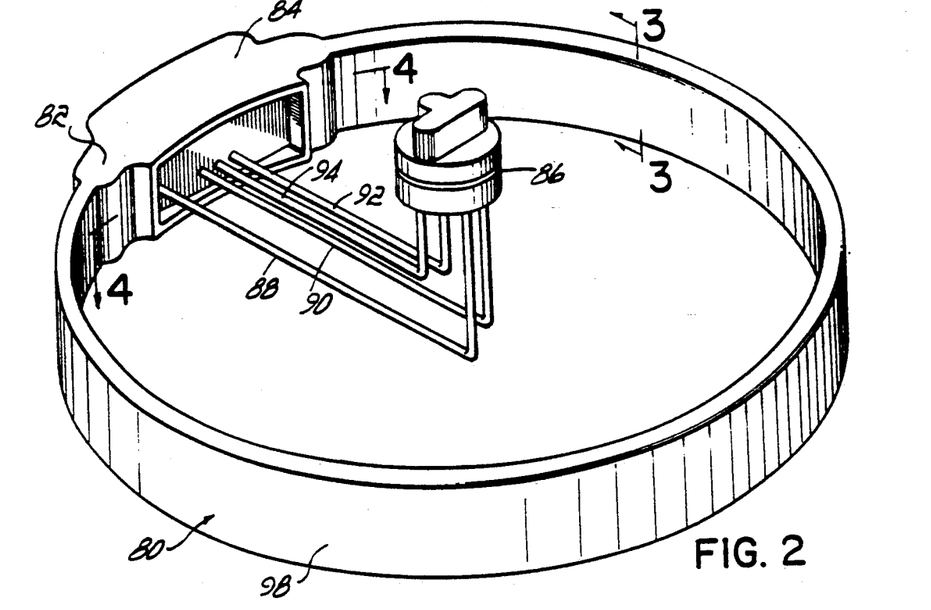
FIG. 2 is a perspective view of an IBM/Cobe 2997 centrifugal apheresis device, for use in this invention.
Figures 3, 4:
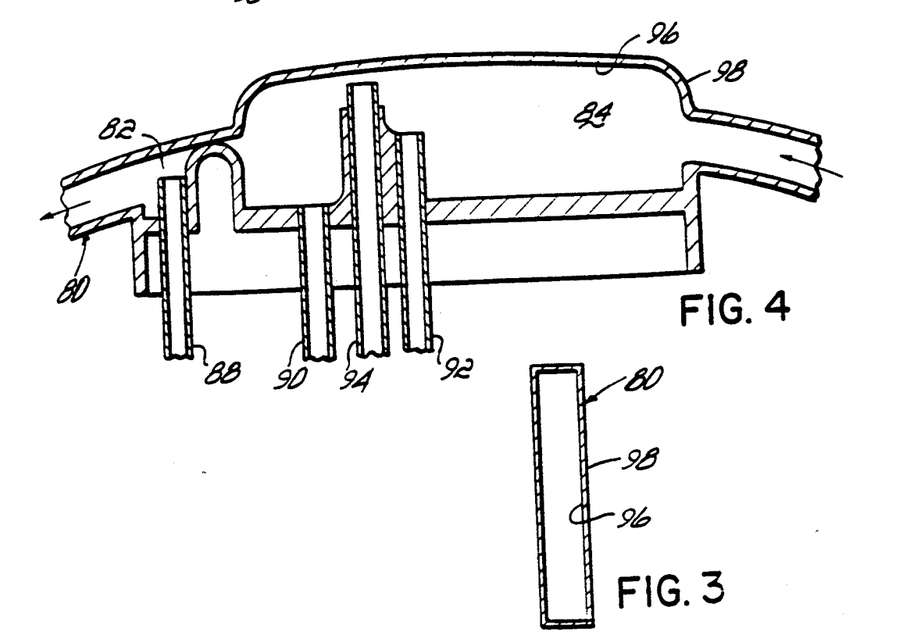
FIG. 3 is a cross-sectional view of the channel of the IBM/Cobe 2997 centrifugal apheresis device of FIG. 2.
FIG. 4 is a longitudinal sectional view of the tubes, input chamber and collection chamber of the IBM/Cobe 2997 centrifugal apheresis device of FIG. 2.

The preferred continuous centrifugal apheresis devices for practicing this invention are a Fenwal Automated Systems Autopheresis-C equipped with a Plateletcell separation device, modified, as described below, and as shown in FIG. 1 and an IBM/Cobe 2997, as shown in FIGS. 2-4. However, the methods of this invention may employ any centrifugal apheresis device modified or developed to provide for removal of separated fluorochemical from the device to prevent buildup in the device. Preferably, the centrifugal apheresis device also operates at a low extracorporeal processing volume so that the amount of blood circulating extracorporeally is minimized. Preferably, the extracorporeal processing volume is as low as possible, i.e., below 200 ml.

DEFINITION OF TERMS a) "fluorochemicals" include highly fluorinated compounds, partially fluorinated compounds and perfluorinated compounds previously said to be useful as oxygen transport agents, "artificial bloods" or "red blood cell substitutes" and contrast agents for biological imaging, for example, perfluorocarbons, partially fluorinated hydrocarbons, and derivatives or mixtures thereof. Such compounds include, inter alia, the 9-18 carbon perfluorohydrocarbons like perfluorodecalin, perfluordimethyldecalin, perfluoromethyldecalin, perflurophenanthrene, perflurodimethyethylcyclohexane, perfluorotrimethylbicyclo(3.3.1)nonane, perfluorodimethyladamantane, perfluoromethyladamantane and perfluoro-2,2,4,4-tetrametylpentane; 9-12 carbon perfluoroamines, such as perfluorotripropylamine, perfluorotributylamine, perfluoro-1-azacyclic amines and F-4-methyloctahydroquinolidizine, perfluorinated ethers (cyclic and alicyclic) such as F-1,5,9-trioxacyclododecane and F-15-crown-5; and halogenated perfluorochemicals, such as perfluorooctylbromide. Suitable fluorochemicals also include F-nonyl-hydride chlorinated perfluorochemicals which include, but are not limited to, monochlorinated perfluorochemicals (e.g. perfluoromonochlorononane), dichlorinated perfluorochemicals (e.g. perfluorodichlorooctanes such as 1,8,dichlorooctane), and trichlorinated perfluorochemicals (e.g. perfluorotrichloroheptane). Of course, mixtures of any highly fluorinated organic compounds may also be separated by the methods of this invention.

Preferably, the fluorochemicals used in the present invention are in the form of emulsions. Fluorochemical emulsions which may be used in the present invention are described in U.S. Pat. No. 3,962,439, U.S. Pat. No. 4,252,827, European Patent Publication 0,231,070, European Patent Publication 231 091 and PCT Publication WO 89/10118. It is to be understood, however, that the present invention is not limited to these fluorochemical emulsions or to any other particular fluorochemical emulsions.

b) "fluorochemical" therapeutically acceptable levels" of reduction refers to a reduction in fluorocrit to below about 5%.

c) "clinically useful quantity or quantities" of fluorochemical-containing whole blood refers to that amount of whole blood contained in the patient being treated, which in a typical (adult) human body is about five liters of whole blood. It is to be understood that one of the advantages of the present invention is that the continuous removal of fluorochemical from a continuous centrifuge to prevent its buildup therein, allows for the useful separation of fluorochemical from the blood of humans and most animals. Preferably the animal treated has a minimum blood volume based on a body weight of at least about 4 kilograms.

d) "centrifugal apheresis devices" refers to devices that are designed, developed, adapted or modified to separate natural components of blood into component-enriched fractions by operation of spinning whole blood at accelerated speed. Such devices include conventional plateletpheresis devices that separate whole blood by action of centrifugal force into plasma-rich and platelet-rich fractions. Such devices generally separate the components of whole blood based on relative density with the densest component being spun to the furthest radial point from the center of rotation. Devices specifically designed to separate fluorochemicals from the natural components of whole blood via continuous centrifugation are also considered to be within the scope of this invention.

e) "continuous" centrifugal apheresis devices refers to devices that operate in a single cycle. Such devices are distinguished from batch devices that employ separate draw cycles and return cycles. In a preferred form, continuous centrifugal apheresis devices include devices that receive a flow of fluorochemical-containing whole blood, separate the fluorochemical-containing whole blood into a fluorochemical-enriched fraction and whole blood-enriched fraction, and preferably continuously remove the fluorochemical-enriched fraction and the whole blood-enriched fraction in one uninterrupted cycle.

f) "extracorporeal volume" refers to the volume of blood contained in the centrifugal apheresis device, including all tubing and the centrifuge bowl or separating chamber, during processing. "Therapeutically acceptable extracorporeal volume" refers to a volume of extracorporeal blood that can be safely withdrawn from a surgical, emergency or trauma patient during fluorochemical separation by centrifugal apheresis. The volume that can safely be withdrawn of course depends on the particular patient but preferably the volume is below about 200 mls.

g) "low volume centrifugal apheresis devices" refers to centrifugal apheresis devices that operate at therapeutically extracorporeal volumes.

h) "therapeutically acceptable spin rate" refers to that rate of spin at which a centrifugal apheresis device may be operated that preserves intact the formed elements of the blood white cells, red blood cells, and platelets, e.g., about 750 to 4000 cycles per second.

i) "therapeutically acceptable flow rate" refers to that rate of flow at which fluorochemical-containing whole blood may be safely drawn from a surgical, emergency or trauma patient, or that rate of flow at which a whole blood-enriched fraction may be safely reinfused to such a patient e.g about 40 to 120 ml/min.

j) "anticoagulant" refers to any clinically acceptable substance that prevents the coagulation of blood. It is to be understood that anticoagulants can be either administered to the patient prior to the withdrawal of fluorochemical-containing blood ("in vivo") or added to the fluorochemical-containing blood after it is withdrawn ("ex vivo").

The preferred methods of this invention employ a centrifugal apheresis device that separates dense components, for example, fluorochemicals, from blood in a continuous cycle while maintaining therapeutically acceptable extracorporeal volumes, thus minimizing the risk of hypotensive shock to the trauma, surgical and emergency patient. The preferred methods employ a modified Autopheresis-C or an off-the-shelf IBM/Cobe 2997 centrifugal apheresis device. These two preferred devices incorporate the key aspects of this invention and will be used to provide a non-limiting description of this invention.

A Fenwal Autopheresis-C Plateletcell separation device is modified for continuous processing of fluorochemical-containing blood. We found that the fluorochemical was too viscous for practical separation with an unmodified Fenwal Platelet separation device. The modified Plateletcell separation device 54 is shown in FIG. 1 and constructed as follows. A magnetic drive 70, which powers the rotor 66 during centrifugation, is sized to accommodate the increased viscosity of the fluorochemical-containing whole blood. As the Fenwal device comes from the factory, the magnetic drive is fitted with two sheet metal stampings, each weighing 30-40 grams. Two more stampings constructed of nickel coated cold rolled steel weighing 30-40 grams each, were added to increase the capacity contained in the magnetic drive two-fold. The diameter of the inner tube 78 through which the whole blood-enriched fraction flows during extra corporeal processing was expanded from a diameter of 0.030 inch to 0.068 inch in order to increase the flow rate. The preferred range of diameters of the inner tube 78 is 0.05 to 0.10 inch, although any diameter that permits continuous removal of the whole blood-enriched fraction will suffice.

The modified device 54 operates as follows in a method of this invention. Fluorochemical-containing whole blood from the patient enters the modified device 54 through inlet needle 10. When the anticoagulant is administered ex vivo, the fluorochemical-containing whole blood is then mixed with anticoagulant from anticoagulant source 26. The anticoagulant is fed into blood line 52, which carries the anticoagulated fluorochemical-containing whole blood to three sites, i.e., the device 54, venous pressure and device pressure lines (not shown). The anticoagulated fluorochemical-containing whole blood enters the modified device 54 through fluorochemical-containing whole blood line 52 by action of blood pump 16 at a preferred rate of about 40 to 120 ml/minute. The fluorochemical-containing whole blood may be pumped into device 54 at any therapeutically acceptable flow rate. The actual rate will vary during each run. The range of therapeutically acceptable rates is dynamic and should be adjusted while visually monitoring the flow of whitish fluorochemical-enriched fraction into collection bag 50. If red flow into collection bag 50 is perceived, the flow rate should be decreased or the spin rate increased. The adjustments to flow rate necessary to achieve an acceptable separation are conventional and are known to persons familiar with the operation of apheresis devices.

Anticoagulated fluorochemical-containing whole blood from the patient enters the device 54 at inlet port 34. Inside the device 54, the anticoagulated fluorochemical-containing whole blood enters a rotor 66 through rotor inlet ports 68. The rotor 66 is a spinning cylinder that serves as a centrifuge. The rotor 66, powered by magnetic drive 70, is spun at preferred rate of about 1200 to 4000 cps, the most preferred rate being 3600 to 4000 cps. The spin rate of the centrifuge may be set at any therapeutically acceptable spin rate that achieves separation of a fluorochemical-enriched fraction and a whole blood-enriched fraction. The adjustments to spin rate necessary to achieve separation are known to persons familiar with the operation of plasmapheresis devices.

The anticoagulated fluorochemical-containing whole blood flows up the inside of the spinning rotor 66. As it moves into separation zone 76, centrifugal force causes a fluorochemical-enriched fraction to separate from a whole blood-enriched fraction. Because fluorochemical is the densest component in the anticoagulated fluorochemical-containing whole blood, the fluorochemical-enriched fraction is spun to the inside wall of the rotor 80. The less dense whole blood-enriched fraction is spun towards the center of rotation. As separation progresses, the fluorochemical-enriched fraction is continuously pumped by separation device pump 24 out of the rotor through the outwardly located ports 72 at the top of the rotor 66 at a rate of about 5 to 10 ml/min. The fluorochemical-enriched fraction then moves through separation device port 30 and continues through line 56 to collection bag 50. A whole blood-enriched fraction is removed through inwardly located ports 74 near the top of the rotor 66 that open into the inner tube 78. The whole blood-enriched fraction flows down the inner tube 78, exits the separation device 54 at separation device outlet port 36, travels through modified separation device line 58 and is returned into the patient through infusion needle 62 or is collected in whole blood-enriched fraction collection bag 60. Because the fluorochemical-enriched fraction is continuously removed to prevent buildup in device 54, the separation may be continued until the fluorochemical content of the separated whole blood-enriched fraction has been reduced to a therapeutically acceptable level.

In another preferred embodiment of the invention, an IBM/Cobe 2997 centrifugal apheresis device is employed without modification as shown in FIG. 2. Centrifugal apheresis is accomplished within a channel 80 made of a semi-rigid plastic tube of rectangular cross section which is lined with a disposable plastic liner. One end of the channel is attached to an inlet chamber 82 and the other is attached to a collection chamber 84. Inlet chamber 82 and collection chamber 84 are joined to form a closed loop with channel 80. The loop is attached to a rotating seal assembly 86 by four tubes 88, 90, 92 and 94. One tube 88 terminates in the inlet chamber 82. The three other tubes are positioned at different radial locations within collection chamber 84.

Fluorochemical-containing whole blood enters the channel 80 through the whole blood input tube 88 located in the inlet chamber 82. As the fluorochemical-containing whole blood progresses circumferentially through the channel, the densest component, fluorochemical, is spun to the inner surface 96 of the outer wall 98 of the channel 80 as shown in FIG. 3. A fluorochemical-enriched fraction thus separates from a whole blood-enriched fraction during the accelerated progression from the inlet chamber 82 to the collection chamber 84. In the collection chamber 84, the fluorochemical-enriched fraction is removed by the lowest radially located tube 94 whereas the whole blood enriched fraction is removed by the higher radially located tubes 90 and 92. Removal of the fluorochemical-enriched fraction is again continuous, allowing for clinically useful separation. Like the embodiment of FIG. 1 employing a modified Autopheresis centrifugal apheresis device, when an IBM/Cobe 2997 device of FIGS. 2-4 is used, the flow rate into the device and the centrifugal spin rate in the channel 80 are adjusted to maintain a continuous flow of whitish fluorochemical-enriched fraction to a collection bag. For the IBM/Cobe 2997, the preferred range of flow rates is 40 to 80 ml/min. and the preferred range of spin rates is 750 to 1250 cps. Any rate that accomplishes separation and preserves intact the red and white blood cells and platelets is acceptable. Persons familiar with the conventional operation of the IBM/Cobe 2997 as a plasma-pheresis device will possess the ordinary skill necessary to adjust the flow and spin rates to achieve separation of a fluorochemical-enriched fraction from fluorochemical-containing whole blood.

In addition to providing for continuous removal of fluorochemical from whole blood, the preferred methods of this invention maintain low extracorporeal blood volumes during processing. The processing volume in the separation device 54 is only 50 to 70 ml. The IBM/Cobe 2997 channel 80 has a 190 ml processing volume.

The methods of the present invention can successfully separate fluorochemical from mixtures of fluorochemical and whole blood having initial fluorochemical content of from about 4% to about 20% by volume, and possibly as high as about 30%. The preferred methods of this invention also minimize the loss of red blood cells. Preferably, 80% or more of the red blood cells in the processed fluorochemical-containing whole blood are recovered. When the fluorochemical has been administered in emulsion form, all of the types of surfactant useful in the preparation of physiologically acceptable fluorochemical emulsions generate emulsions that can be separated from blood by the methods of centrifugal apheresis described in this invention. Examples of acceptable surfactant include, but are not limited to, lecithins, pluronics and fluorosurfactants. Any anticoagulation regime should suffice for the methods of this invention such as citrate or heparin.

The methods of this invention are useful for removing fluorochemicals from blood after they have been administered in a variety of medical applications. These include, but are not limited to, use in emergency treatment, elective, emergency, and trauma surgery, myocardial infarct treatment, coronary balloon angioplasty, stroke treatment, liquid breathing treatment, intraperitoneal oxygenation, cardio-pulmonary bypass, organ preservation and surgery involving hemodilution.

The following non-limiting examples illustrate various embodiments of this invention.

EXAMPLE 1

A perfluorochemical emulsion containing 1.75 w/v% lecithin, 2 w/v% safflower oil and 40 v/v% perfluorodecalin was mixed with sufficient blood to give five liters of a mixture with a hematocrit of 31.1% and a fluorocrit of 12.6%. In order to simulate the removal of fluorochemical from the blood of a human, the mixture was placed in a 5-liter carboy. The mixture was then processed through separation device 54 of FIG. 1 for continuous removal of fluorochemical. During processing, the whole blood-enriched fraction was returned to the carboy while the fluorochemical-enriched fraction was collected in a waste bag. The flow rate was varied between 40 to 80 ml/min. with a spin rate of 3600 cps. The flow rate was manually varied while a white flow of separated perfluorodecalin was visually monitored as it gathered in the waste bag. Within the 40 to 80 ml/min range, flow was maintained at the highest rate at which only white perfluorodecalin was observed. When red flow was detected in the line to the collection bag, the rate was decreased within the 40 to 80 ml/min range. After 2.5 hours of processing, a final fluorocrit of 4% in the processed blood was achieved. Therefore, 68% of the perfluorochemical had been removed, while less than 2% of the red blood cells had been lost. The final hematocrit of 39.3% demonstrated significant and useful hemoconcentration. Thus, continuous processing removed a significant amount of perfluorochemical from an amount of blood about equal to that in a human. In addition, the method maintained adequate concentrations of red blood cells.

By comparison, in addition to the disadvantage of an unacceptable red blood cell loss, batch centrifugal apheresis by means of a Haemonetics V-50 device, referred to in the background of this invention, is limited by the fact that the centrifuge clogs before a clinically useful quantity of fluorochemical-containing whole blood can be processed. Since the average patient has five liters of blood, and clogging of both centrifuge bowls halted apheresis both times after about one liter of processing, it is clear that the batch-processing Haemonetics V-50 is inadequate for complete removal of fluorochemical from a patient.

EXAMPLE 2

A mongrel dog was made anemic by successive blood exchanges with sodium chloride solution over a four day period. One week later, the anemic 21.2 kg. dog was infused with 40 cc/kg. of an emulsion containing 1.75 w/v% lecithin, 2 w/v% oil and 40 v/v% perfluorooctyl bromide. Four hours after infusion, the dog had a hematocrit of 20.7% and a fluorocrit of 16.7%. The dog was connected to the FIG. 1 device equipped with the separation device 54 via 14 gauge angiocaths in the cephalic veins of the left and right forearms. One arm was used to remove fluorochemical-containing whole blood from the dog while the other arm was used to return the whole blood-enriched fraction at a therapeutically acceptable flow rate after removal of the fluorochemical-enriched fraction. The dog's fluorochemical-containing whole blood was processed through the separation device 54 for approximately two hours after which time its hematocrit was 16.8% and its fluorocrit was 3.4%, representing more than a 79% reduction in fluorocrit. The dog survived and lived normally until a scheduled sacrifice.

EXAMPLE 3

A naive 21.6 kg. mongrel dog with a normal hematocrit of 40.0 was infused with 40 cc/kg of the same emulsion described in Example 2. Four hours after infusion, the dog had a hematocrit of 40% and a fluorocrit of 14.1%. The dog was apheresed as in Example 1 for about two hours after which time it had a hematocrit of 33.9% and a fluorocrit of 3.7%. Thus, even in a dog with a high initial hematocrit (which increases the viscosity of the blood-fluorochemical mixtures), excellent reduction of fluorochemical content ($-74\%$) has been achieved, while minimizing loss in hematocrit.

Figure 5:
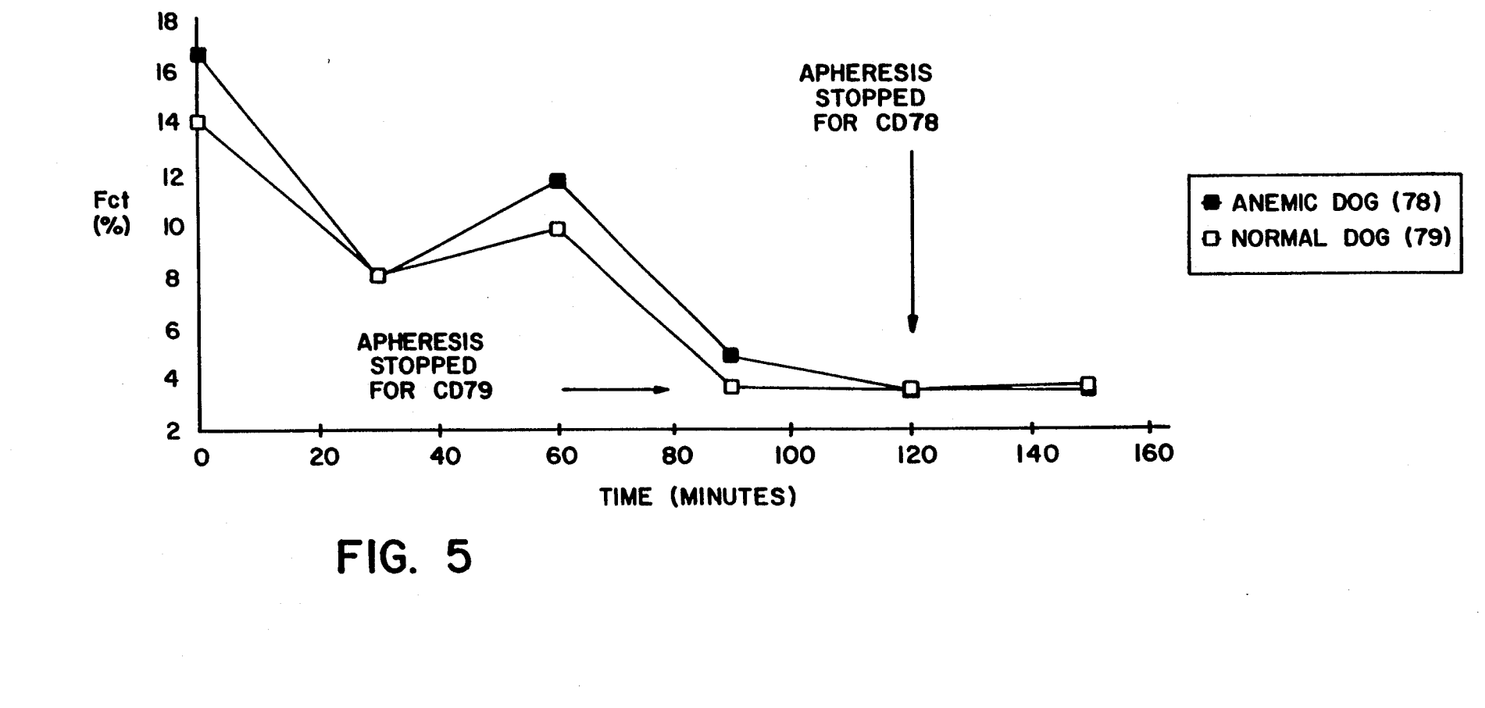
FIG. 5 is a graphic representation of fluorochemical content of the blood of an anemic and a normal dog before, during and after apheresis using the device depicted in FIG. 1.
Figure 6:
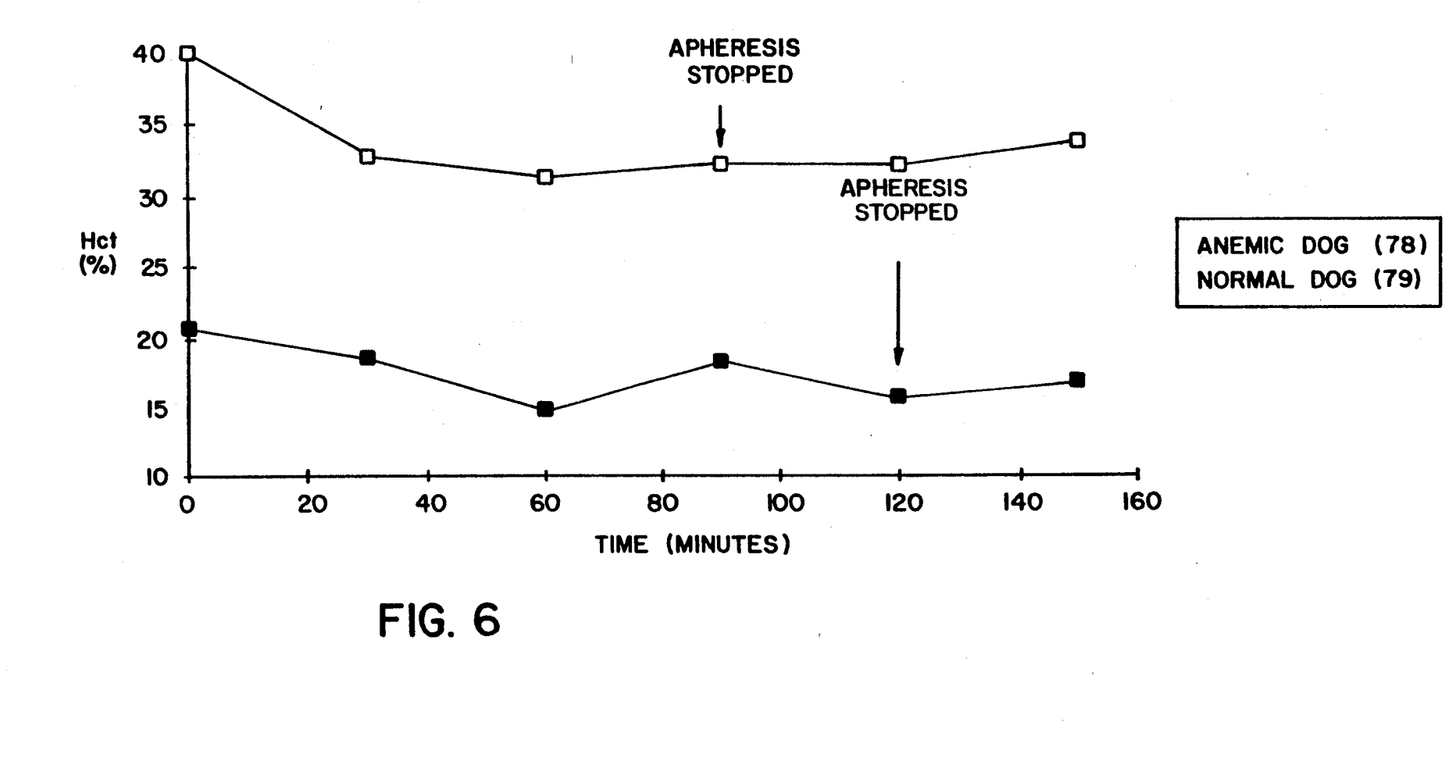
FIG. 6 is a graphic representation of the hematocrit content of the blood of an anemic and a normal dog before, during and after apheresis using the device, depicted in FIG. 1.

The results of apheresis on fluorocrit and hematocrit content of this dog and the anemic dog of Example 2 are depicted graphically in FIG. 5 and FIG. 6.

EXAMPLE 4

Figure 7:
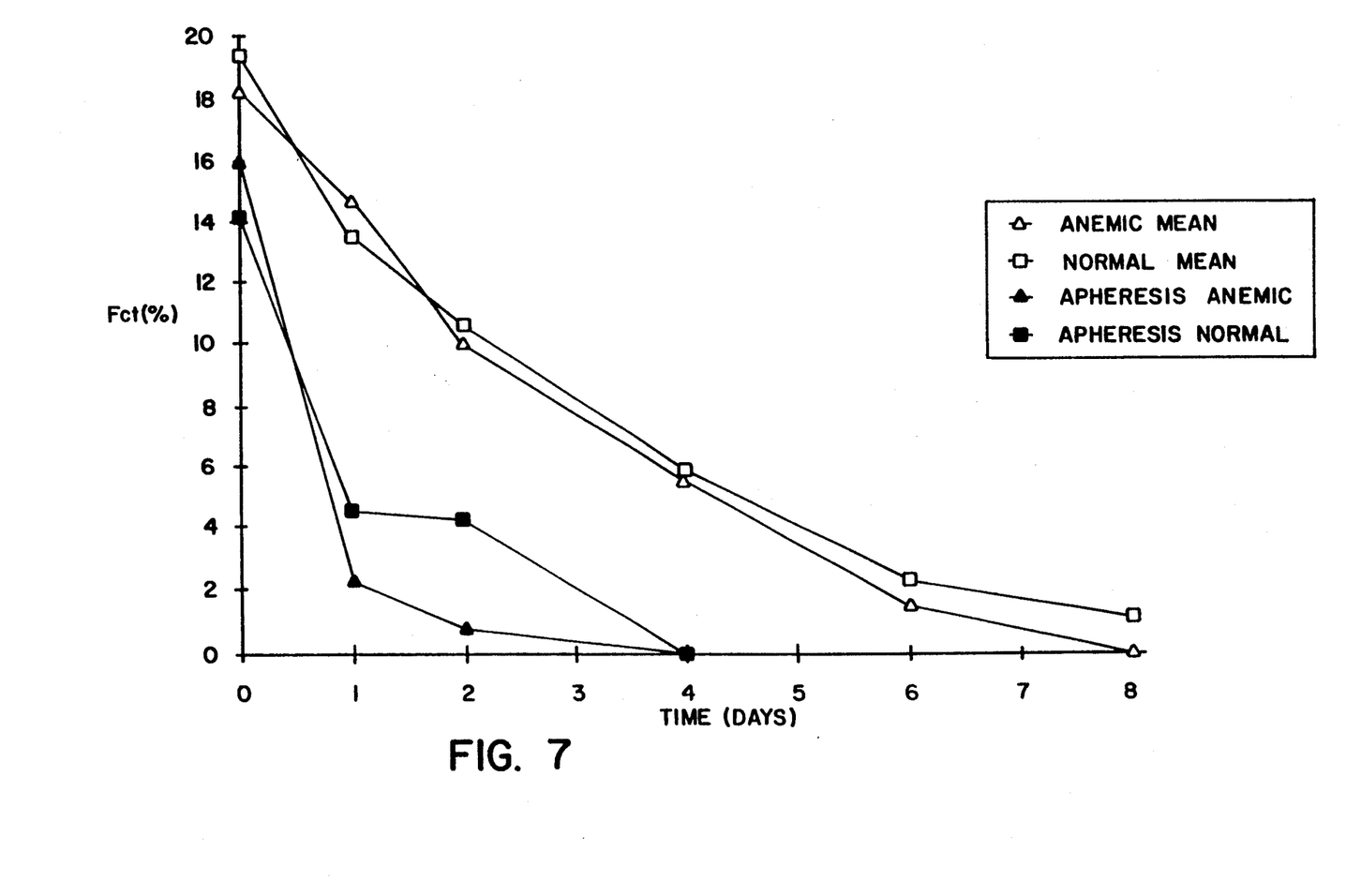
FIG. 7 is a graphic representation of the reduction in fluorochemical content in the blood of anemic and normal dogs infused with 40 cc/kg fluorochemical emulsion then apheresed four hours later using the device depicted in FIG. 1, compared with similarly infused anemic and normal dogs that were not apheresed.
Figure 8:
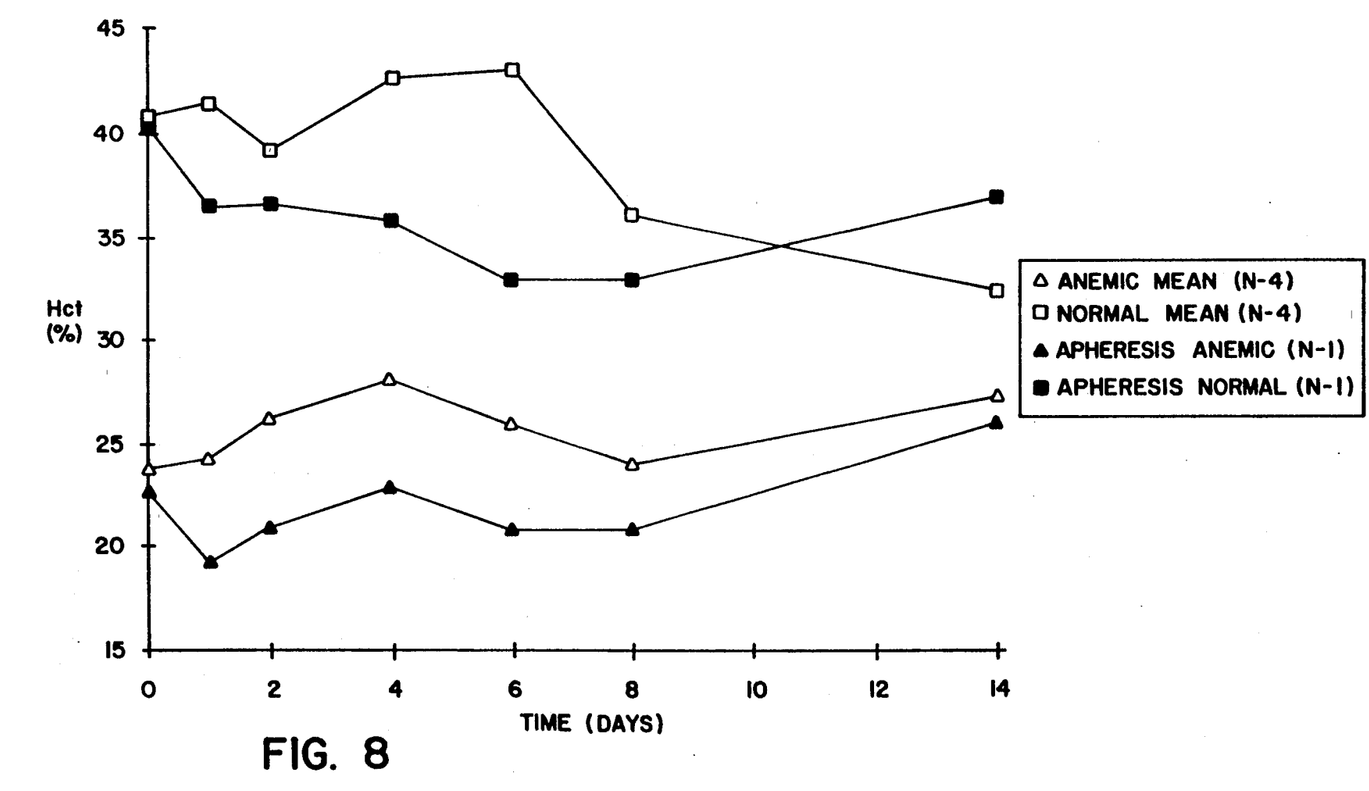
FIG. 8 is a graphic representation of the hematocrit content in the blood of anemic and normal dogs infused with 40 cc/kg fluorochemical emulsion then apheresed four hours later, using the device depicted in FIG. 1, compared with similarly infused anemic and normal dogs that were not apheresed.

Four anemic dogs and four naive dogs were each infused with 40 cc/kg of the same fluorochemical emulsion used in Examples 2 and 3. The animals were not apheresed and were monitored over an 8-day period as were the apheresed dogs of Examples 2 and 3. As shown in FIG. 7, the fluorocrits of the apheresed dogs of Examples 2 and 3 were reduced to below a detectable amount by the fourth day post infusion. The non-apheresed dogs (both anemic and naive), which eliminated fluorochemical through natural excretion, continued to have detectable levels of fluorochemical in their blood up through 8 days post-infusion. As shown by FIG. 8, apheresis accomplished the removal of fluorochemical without significant decrease in hematocrit.

The benefits of apheresis over natural excretion are also demonstrated by Table 1 below, which sets forth the fluorochemical content of the organs of apheresed and non-apheresed dogs at 14-days post infusion.

TABLE 1

Perfluorochemical (PFC) content in the organs of apheresed and non-apheresed dogs at fourteen days post infusion of 40 cc/kg PFC emulsion.

| PFC CONTENT (% Dose) | Anemic Apheresed | Normal Apheresed | Anemic and Normal Non-apheresed |
|---|---|---|---|
| Lung | 0.01% | 0.02% | 1% |
| Liver | 3% | 10% | 41% |
| Spleen | 5% | 5% | 14% |

EXAMPLE 5

A 40 v/v% perfluorodecalin emulsion was prepared as in Example 1 to give five liters of a mixture with a hematocrit of 28.2% an a fluorocrit of 12.3%. This mixture was processed through an IBM/Cobe 2997 plasma-pheresis unit of FIG. 2 at a flow rate that varied between 40 and 80 ml/min. with a spinning rate of 750–1250 cps. After 1.5 hours of processing, 60% of the perfluorochemical had been removed (final fluorocrit 4.9%) while less than 2% of the red blood cells had been lost. The final hematocrit was 24%. Thus, continuous processing using an IBM/Cobe 2997 allowed processing of blood on a scale comparable to human blood volumes at medically useful concentrations of red blood cells and perfluorochemical.

Other variations or embodiments will become apparent to one of ordinary skill in using this art in view of the above description and such are within the scope of this invention.

What is claimed is:

1. A method of extracorporeally removing fluorochemical from fluorochemical-containing whole blood of a patient comprising withdrawing a therapeutically acceptable extra-corporeal volume of the fluorochemical-containing whole blood from the patient, passing the withdrawn blood through a continuous centrifugal apheresis device for removal of the fluorochemical and return of the blood to the patient at a therapeutically acceptable flow rate, centrifugally separating at a therapeutically acceptable spin rate the withdrawn blood in the device into a fluorochemical-enriched fraction and a whole blood-enriched fraction, removing the fluorochemical-enriched fraction from the centrifuge device to prevent build up of fluorochemical in the device, and returning the whole blood-enriched fraction to the patient wherein said method takes place during one continuous cycle.

2. The method of claim 1 comprising continuously removing the fluorochemical-enriched fraction and whole blood-enriched fraction from the centrifuge device during one uninterrupted cycle.

3. The method of claim 1 wherein the retained volume of withdrawn blood in the device is below about 200 ml.

4. The method of claim 3 comprising introducing the whole blood into the device at a flow rate in the range of about 40 to about 120 ml/min.

5. The method of claim 3 comprising operating the device at a spin rate of about 750 to about 4000 cycles per second.

6. The method of claim 1 wherein the fluorochemical is present in the whole blood of the patient in a clinically useful quantity.

7. The method of claim 6 wherein the fluorochemical is present in an amount of about 4% to about 30% by volume.

8. The method of claim 1 wherein the returned whole blood-enriched fraction has a fluorocrit reduced to a therapeutically acceptable level.

9. The method of claim 8 wherein the fluorocrit is reduced to below about 5%.

10. The method of claim 1 wherein the fluorochemical is selected from the group consisting of any one or a mixture of perfluorodecalin, perfluorodimethyldecalin, perfluoromethyldecalin, perfluorotrimethylbicyclo(3.3.1.)nonane, perfluorodimethyladamantane,perfluoromethyladamantane, perfluoro-2,2,4,4-tetramethylpentane, perfluorotripropylamine, perfluorotributylamine, perfluoro-1-azacyclic amines, F-4-methyl-octahydroquinolidizine, perfluoro-1,5,9-trioxacyclododecane, perfluoro-15-crown-5, perfluorooctylbromide, perfluorodichlorooctane, perfluoromonochlorononane perfluorononyl-hydride, perfluorophenanthrene, F-dimethylethylcyclohexane and perfluorotrichloroheptane.

11. The method of claim 1 wherein the fluorochemical-containing whole blood is treated with an anticoagulant prior to centrifuging.

12. The method of claim 1 comprising separating natural components of the withdrawn blood into component-enriched fractions by operating said device at accelerated speeds.

* * * * *